US00PP36532P2

(12) United States Plant Patent
Hansen

(10) Patent No.: US PP36,532 P2
(45) Date of Patent: Mar. 4, 2025

(54) X MANGAVE PLANT NAMED 'Living on a Prayer'

(50) Latin Name: ***Manfreda* x *Agave* hybrid**
Varietal Denomination: Living on a Prayer

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 18/445,827

(22) Filed: Feb. 23, 2024

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
CPC ... A01H 5/12; A01H 5/00; A01H 5/02; A01H 6/12
See application file for complete search history.

(56) References Cited

U.S. PATENT DOCUMENTS

PP34,508 P2 * 8/2022 Hansen ..... A01H 6/12 Plt./373

* cited by examiner

*Primary Examiner* — June Hwu

(57) ABSTRACT

A new and unique X *Mangave* plant named 'Living on a Prayer' characterized by habit that is a rounded mound and becomes globose to pyriform-shaped in maturity. The numerous lanceolate leaves are dark olive-green with marbled white to whitish-green and have large, firm, deep wine-colored apical mucro and thin reddish-brown margins and small marginal teeth. The new plant is suitable as a potted houseplant plant, as a container plant for the patio or garden and for the garden or planted in the landscape.

1 Drawing Sheet

Botanical classification: *Manfreda* x *Agave* hybrid.
Variety denomination: 'Living on a Prayer'.

CROSS-REFERENCE TO RELATED APPLICATIONS

X *Mangave* plant named 'Hope and a Prayer' U.S. Plant patent application Ser. No. 18/445,828; X *Mangave* plant named 'Artistic Liberty' U.S. Plant Pat. No. 36,192.

STATEMENT REGARDING PRIOR DISCLOSURES UNDER 37 CFR 1.77(b)(6)

No plants of x *Mangave* 'Living on a Prayer' have been sold, offered for sale, or disclosed in this country or anywhere in the world as of this filing.

BACKGROUND OF THE INVENTION

The present invention relates to the new and distinct X *Mangave* plant, X *Mangave* 'Living on a Prayer' discovered on Jan. 30, 2023, by the inventor in a greenhouse at a wholesale perennial nursery in Zeeland, Michigan, USA as whole plant mutation in a tissue cultured batch of 'Praying Hands' U.S. Plant Pat. No. 34,508. Through trials at the same nursery the plant was referred to by the code 23-SP-MANG-1193A. The new plant has been successfully asexually propagated initially by division of pups in early 2024, and also by shoot tip tissue culture at the same nursery in Zeeland, Michigan. This asexual propagation system has been found to produce stable and identical plants that maintain all the unique characteristics of the original plant in successive generations.

BRIEF SUMMARY OF THE INVENTION

X *Mangave* 'Living on a Prayer' differs from its parents as well as all other *Manfreda, Agave* and x *Mangave* known to the applicant. The most similar x *Mangave* cultivars known to the inventor are: 'Artistic Liberty' U.S. Plant Pat. No. 36,192, *Agave simplex* 'Snow Devil' (not patented), 'Sweet Tooth' U.S. Plant Pat. No. 34,255, *Agave potatorum* 'Lonkie' (not patented), and x *Mangave* 'Hope and a Prayer' U.S. Plant Patent Application copending.

'Artistic Liberty' has a more glaucous, oblanceolate to rhombic foliage with larger marginal teeth, less globe-like habit with foliage apices that are more extrorse or more divergent, and the variegation is spread throughout the leaf surface rather than in the center. 'Snow Devil' has a more horizontal and extrose foliage habit, leaves that are more ovate, leaf apices that are more extrorse, leaves that lack mahogany spotting, and larger marginally toothed. 'Sweet Tooth' has a more horizontal and extrose foliage habit, the leaves have larger more prominent marginal teeth that start pale yellow and transition to reddish orange before maturing to a dark reddish, and the green variegation is confined to just the margin and the marbling to the leaf interior. 'Lonkie' has more rhomboidal foliage that is more extrorse, with larger marginal teeth, and the center variegation has striations of light grayish-green and cream. 'Hope and a Prayer' has a yellowish-green marginal variegation rather than the marbled white to whitish-green.

The parent lacks the green with white to whitish-green variegation of the foliage.

The new plant, 'Living on a Prayer', is unique from all of these *Agave*, X *Mangave* and *Manfreda* known to the inventor by the following combined traits:

1. Rounded, mounded, with foliage curving upwardly and toward the center, becoming globose to pyriform with maturity;
2. Foliage is lanceolate, slightly cupped distally, of dark olive-green color that is marbled with white to whitish-green, developing reddish-purple spots with high ultraviolet light exposure;
3. Leaves have small, short, sharp, marginal teeth and long, stiff, deep wine-colored apical mucro;
4. Leaves have thin reddish-brown margins and complementing apical mucro;
5. Moderate growth rate.

BRIEF DESCRIPTION OF THE DRAWINGS

The photograph of the new plant demonstrates the overall appearance of 'Living on a Prayer' including the unique traits as a one-year-old plant grown in a partially shaded greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
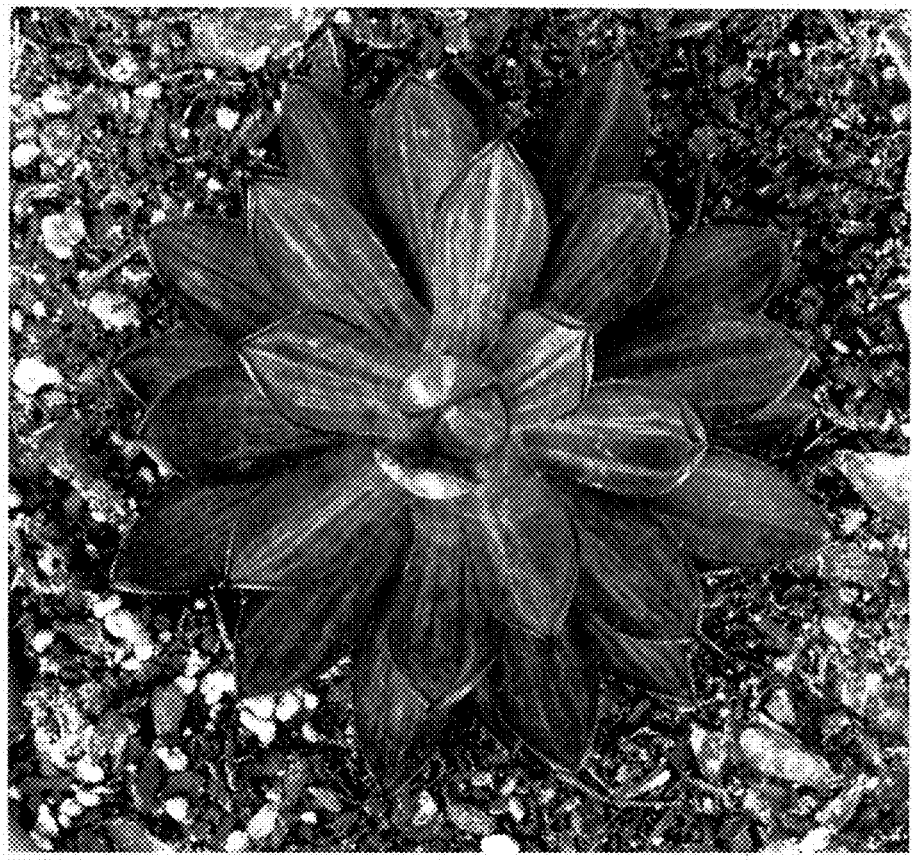
FIG. 1 shows the habit of the new plant from above.
Figure 2:
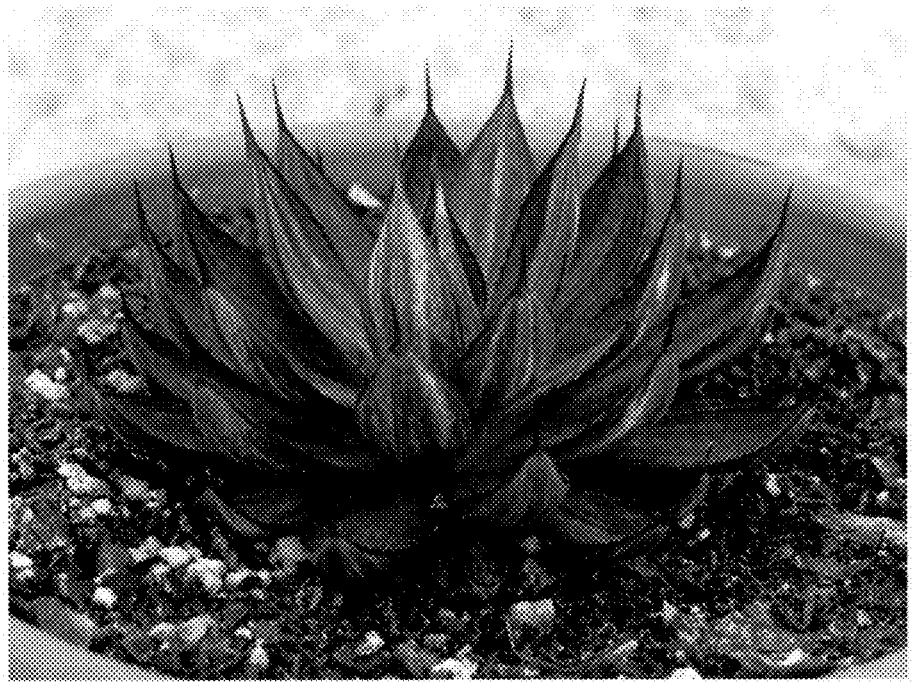
FIG. 2 shows the habit of the new plant from the side.

The following descriptions and color references are based on the 2015 edition of The Royal Horticultural Society Colour Chart except where common dictionary terms are used. The new plant, X *Mangave* 'Living on a Prayer', has not been observed under all possible environments. The phenotype may vary slightly with different environmental conditions, such as temperature, light, fertility, moisture and maturity levels, but without any change in the genotype. The following observations and size descriptions are of one-year-old plants in a commercial wholesale greenhouse in Zeeland, Michigan with supplemental water and fertilizer as needed.

Botanical classification: x *Mangave* hybrid (*Manfreda* x *Agave*);

Parentage: A whole plant mutation of 'Praying Hands';

Propagation: Sterile plant tissue culture;

Time to initiate roots from tissue culture: About 28 days;

Growth rate: Moderate;

Crop time: About 22 to 26 weeks to finish during lengthening spring days from an established 25 mm tissue culture plug to a 65 mm diameter container;

Rooting habit: Fleshy, lightly branching, with roots up to 35 cm long and typically 3 mm diameter;

Root color: Nearest RHS 155D;

Plant shape and habit: Succulent herbaceous perennial with basal rosettes of about 34 fleshy leaves emerging outwardly from short stem and slightly arching upwardly and introrse toward apices, producing a symmetrical, rounded, globose, mound;

Plant size: Foliage height about 8 cm tall from soil line to the top of the leaves and 12.5 cm wide at about 5 cm above soil level;

Foliage description: Lanceolate; simple; sarcous; glabrous; fibrous; moderately lustrous adaxial and abaxial; margins dentate with small short teeth curling toward leaf base; apex acute with long firm mucro; base truncate, sessile, clasping; slightly cupped toward apex; curved outwardly near base and upwardly and introrse toward apex;

Leaf size: To about 6 cm long, about 2.2 cm wide in the widest portion about one-third from apex, basal portion flared to about 2 cm wide at attachment, and 0.6 cm thick at base;

Marginal teeth: Flattened top to bottom; very small, about 0.1 mm long and 0.5 to 1 mm wide; proximally concentrated, to about 3 mm apart; distally void;

Foliage fragrance: None observed;

Leaf blade color:

*Adaxial*.—Young between RHS 136A and RHS NN137A with irregular longitudinal streaks of white to light green distally between RHS NN155B and RHS NN155C and proximally between RHS 142D and RHS 145D that also contain variably-sized fragments of green between 0.2 mm diameter and 0.5 mm across and 6 mm long between RHS 136A and RHS NN137A, without significant reddish-purple spotting; mature nearest RHS NN137A with irregular longitudinal white streaks of nearest RHS NN155C and nearest RHS 157D that also contain variably-sized fragments of green nearest RHS 137A between 0.2 mm diameter and 0.5 mm across and 6 mm long colored, and faint random spotting between 2 mm to 4 mm diameter in lower ultraviolet light of nearest RHS 186C;

*Abaxial*.—Young between RHS 136B and RHS NN137B with irregular longitudinal streaks of white to light green distally between RHS NN155B and RHS NN155C that also contain fragments of green between RHS 136B and RHS NN137B and random spotting between 2 mm and 4 mm diameter of nearest RHS 186C; mature between RHS NN137B and RHS 136B with irregular longitudinal streaks of white to light green distally between RHS NN155B and RHS NN155C that also contain fragments of green between RHS 136B and RHS NN137B and random spotting between 2 mm and 4 mm diameter of nearest RHS 186C;

*Teeth and edge color*.—Young adaxial and abaxial distally between RHS 173B and RHS 174A, proximally nearest RHS 138D, mature adaxial and abaxial distally nearest RHS 176A and proximally nearest RHS 138D.

Mucro: Firm; sharp; straight, about 9 mm long and 1.5 mm across at base;

Mucro color: Young between RHS 172A, RHS 172B and RHS 187B, mature nearest RHS 202A;

Petiole: Sessile;

Veins: Parallel; not distinct;

Flower description: Flowers not yet observed;

Fruit: Not yet observed;

Seed: Not yet observed;

Disease resistance: x *Mangave* 'Living on a Prayer' has not been observed to be resistant or susceptible to diseases common to other x *Mangave* beyond that which is normal for *Agave* or *Manfreda*. The plant is xeromorphic and survives well with minimal water once established. Hardiness at least from USDA zone 9 to 11. The full extent of winter hardiness has not been tested.

I claim:

1. A new and distinct cultivar of ornamental X *Mangave* plant named 'Living on a Prayer' as herein described and illustrated.

* * * * *